US006869404B2

(12) United States Patent
Schulhauser et al.

(10) Patent No.: US 6,869,404 B2
(45) Date of Patent: Mar. 22, 2005

(54) APPARATUS AND METHOD FOR CHRONICALLY MONITORING HEART SOUNDS FOR DERIVING ESTIMATED BLOOD PRESSURE

(75) Inventors: Randal C. Schulhauser, Phoenix, AZ (US); Gary Stefanov, Mississauga (CA); Jon S. Tracy, Orangeville (CA); Eric M. Rieder, Georgetown (CA); Mark Son, Etobicoke (CA); Brian B. Lee, Golden Valley, MN (US); Nicole M. Haupt, Etobicoke (CA)

(73) Assignee: Medtronic, Inc., Minneapolis, MN (US)

( * ) Notice: Subject to any disclaimer, the term of this patent is extended or adjusted under 35 U.S.C. 154(b) by 190 days.

(21) Appl. No.: 10/376,063

(22) Filed: Feb. 26, 2003

(65) Prior Publication Data

US 2004/0167417 A1 Aug. 26, 2004

(51) Int. Cl.$^7$ ................................................. A61B 5/02
(52) U.S. Cl. ..................................................... 600/528
(58) Field of Search ................................. 600/504, 508, 600/513, 518, 526–528; 607/17, 36

(56) References Cited

U.S. PATENT DOCUMENTS

| 5,117,824 | A | 6/1992 | Keimel et al. |
| 5,313,953 | A | 5/1994 | Yomtov et al. |
| 5,535,752 | A | 7/1996 | Halperin et al. |
| 5,987,352 | A | 11/1999 | Klein et al. |
| 6,230,059 | B1 | 5/2001 | Duffin |
| 6,351,670 | B1 | 2/2002 | Kroll |
| 6,409,675 | B1 | 6/2002 | Turcott |
| 6,477,406 | B1 * | 11/2002 | Turcott ...................... 600/518 |
| 2004/0167416 | A1 * | 8/2004 | Lee ............................ 600/513 |

FOREIGN PATENT DOCUMENTS

WO     WO 90/04942 A1     5/1990

OTHER PUBLICATIONS

Chen, D.,et al., "Estimation of Pulmonary Artery Pressure by Spectral Analysis of the Second Heart Sound", *American Journal Cardiology*, 1996; vol. 78, pp. 785–789.

Adams, K., "Guiding Heart Failure Care by Invasive Hemodynamic Measurements: Possible or Useful?", *Journal of Cardiac Failure*, vol. 8, No. 2, 2002, pp. 71–73.

Bartels, A., et al., "Non–invasive Determination of Systolic Blood Pressure by Heart Sound Pattern Analysis", *Clin. Phys. Physiol. Meas.*, 1992, Aug.; 13(3), pp. 249–256.

Xu, J., et al., "A New, Simple and Accurate Method for Non–Invasive Estimation of Pulmonary Arterial Pressure", *Heart*, 2002, vol. 88, pp. 76–80.

Gulcur, H., et al., "Estimation of Systolic Blood Pressure from the Second Heart Sounds", *IEEE*, 1997, pp. 39–41.

* cited by examiner

*Primary Examiner*—George Manuel
(74) *Attorney, Agent, or Firm*—Girma Wolde-Michael; Michael C. Soldner

(57) ABSTRACT

A minimally invasive, implantable heart sound and ECG monitor and associated method for deriving blood pressure from heart sound data. The device is equipped with an acoustical sensor for detecting first and second heart sounds which are sampled and stored during sensing windows following R-wave and T-wave detections, respectively. ECG and heart sound data are stored in a continuous, looping memory, and segments of data are stored in long-term memory upon an automatic or manual data storage triggering event. Estimated blood pressure is calculated based on custom spectral analysis and processing of the first and second heart sounds. A calibration method includes measuring a patient's blood pressure using a standard clinical method and performing regression analysis on multiple spectral variables to identify a set of best fit weighted equations for predicting blood pressure. Concurrent ECG and estimated blood pressure may be displayed for review by a physician.

20 Claims, 8 Drawing Sheets

APPARATUS AND METHOD FOR CHRONICALLY MONITORING HEART SOUNDS FOR DERIVING ESTIMATED BLOOD PRESSURE

CROSS-REFERENCE TO RELATED APPLICATION

Cross-reference is hereby made to commonly assigned related U.S. application Ser. No. 10/376,062, filed concurrently herewith, entitled "METHOD AND APPARATUS FOR MONITORING HEART FUNCTION IN A SUBCTANEOUSLY IMPLANTED DEVICE".

FIELD OF THE INVENTION

The present invention relates to implantable medical devices and, in particular, to a minimally invasive implantable device for monitoring a patient's blood pressure by recording heart sounds and deriving an estimated blood pressure based on custom heart sound spectral analysis and processing.

BACKGROUND OF THE INVENTION

Blood pressure monitoring is a fundamental diagnostic tool for a wide array of cardiovascular and other pathologic conditions. Systolic and diastolic blood pressure may be measured indirectly and non-invasively using a standard cuff method. However, direct monitoring of blood pressure is sometimes desired for diagnosing or tracking a disease state using relatively invasive measurement methods that use an indwelling blood pressure catheter. An indwelling catheter, however, may only remain implanted for relatively acute periods of time to prevent infection or other associated complications. Chronic monitoring of blood pressure could be extremely valuable to a physician in numerous patient monitoring applications, such as monitoring heart failure, hypertension, diabetes, or other infrequent, acute conditions such as unexplained syncope, unexplained seizures, etc.

Chronic blood pressure monitoring can be performed by placing an implantable pressure sensor directly in the cardiovascular system, such as the right ventricle. An implantable absolute pressure monitoring system is disclosed in U.S. Pat. No. 5,535,752, issued to Halperin, et al. A chronically implantable device for monitoring the intracardiac electrogram (EGM) and right ventricular blood pressure has been implanted in chronic heart failure patients and used to continuously monitor their hemodynamic condition. See Magalski A, et al., J. Card. Fail., 2002;8(2):71–3. Apparatus for monitoring for syncope including electrodes for recording electrical activity and/or blood pressure data of the patient's heart is disclosed in U.S. Pat. No. 6,351,670 issued to Kroll. An ambulatory cardiac diagnostic unit is disclosed in PCT Publication No. WO 90/04942, issued to Baker et al., which monitors heart action using intracardiac electrogram and pressure sensed using an intracardiac lead. These systems advantageously provide chronic blood pressure monitoring but involve placement of a lead within the patient's heart.

Placement of a pressure sensor directly in the heart or cardiovascular system is a relatively invasive procedure with associated risks and complications. Therefore, it is desirable to provide a device and method for chronically monitoring blood pressure that is a simple to implant, relatively non-invasive device. Indirect methods of measuring blood pressure allow a sensor to be placed outside of the cardiovascular system and the measured signal may be correlated to blood pressure.

FIG. 1 is a graphical representation of simultaneous ECG events, blood pressure changes and heart sounds that occur in the left ventricle during a cardiac cycle. Ventricular systole begins when an action potential conducts through the atrioventricular node (AV node) and quickly depolarizes the ventricular myocardium. This event is distinguished by the QRS complex on the ECG. As the ventricles contract, pressure in the ventricles begins to rise, causing abrupt closure of the mitral and tricuspid valves between the ventricles and atria as ventricular pressure exceeds atrial pressure. As illustrated in FIG. 1, this valve closure generates the first heart sound, $S_1$, at the start of ventricular systole. $S_1$ generally has a duration of about 150 ms and a frequency on the order of 25 to 45 Hz. In FIG. 1, left ventricular pressure (LVP) is seen to rise dramatically following the QRS complex portion of the ECG and closure of the mitral valve.

The ventricular pressure continues to build until the aortic and pulmonary valves open, ejecting blood into the aorta and pulmonary artery. In FIG. 1, aortic pressure is seen to rise with left ventricular pressure after opening of the aortic valve. Ventricular contraction continues to cause blood pressure to rise in the ventricles and the aorta and pulmonary artery. As the contraction diminishes, blood pressure decreases until the aortic and pulmonary valves close. Aortic pressure typically reaches a maximum of 120 mmHg during ventricular systole and a minimum of 80 mmHg during ventricular diastole. The second heart sound, $S_2$, corresponds to closure of the aortic and pulmonary valves, near the end of ventricular systole and start of ventricular diastole. $S_2$ generally has a duration of about 120 ms and a frequency on the order of 50 Hz and will be related to the diastolic pressure in the aorta and the pulmonary artery.

The third heart sound, $S_3$, is associated with early, passive diastolic filling of the ventricles, and the fourth heart sound, $S_4$, is associated with late, active filling of the ventricles due to atrial contraction. The third sound is generally difficult to hear in a normal patient using a stethoscope, and the fourth sound is generally not heard in a normal patient. Presence of the third and fourth heart sounds during an examination using a stethoscope may indicate a pathological condition. Physicians are particularly familiar with evaluating heart sounds as part of a basic physical examination, and a stethoscope is a standard component in a physician's diagnostic tool box.

An extravascular hemodynamic monitor that includes vascular plethysmography, heart and lung sound, thoracic impedance and ECG sensors is generally disclosed in U.S. Pat. No. 6,409,675, issued to Turcott, incorporated herein by reference in its entirety. Phonocardiogram data is stored for later retrieval allowing the physician to review the morphology of the phonocardiogram for signs of acute heart failure exacerbation.

Mathematical models for calculating systolic and diastolic blood pressure based on the frequency and/or amplitude components of the first and second heart sounds have been proposed. See, for example, A. Bartels et al., "Non-invasive determination of systolic blood pressure by heart sound pattern analysis," Clin. Phys. Physiol. Meas., 1992; 13:249–56; D. Chen et al., "Estimation of pulmonary artery pressure by spectral analysis of the second heart sound," Am. J. Cardiology, 1996; 78:785–9; and J. Xu et al., "A new simple and accurate method for non-invasive estimation of pulmonary arterial pressure," Heart, 2002; 88:76–80.

Therefore, chronic monitoring of blood pressure based on heart sounds could provide physicians with a valuable diagnostic tool for detecting and monitoring pathologic conditions, which manifest in abnormal blood pressure responses or changes. For example, syncope, the temporary loss of consciousness due to cerebral ischemia, can be particularly problematic to diagnose because a syncopal event can be sudden, without warning, and may occur very infrequently, rarely under the supervision of an examining physician. Underlying causes of syncope can be associated with cardiac causes, metabolic causes, neurologic causes, and other miscellaneous causes such as coughing, severe pain or vertigo.

Cardiac causes include a group of autonomic disturbances resulting in othostatic intolerance. The heart rate is normally regulated by a balance between the sympathetic and parasympathetic (vagal) components of the autonomic nervous system. Increased sympathetic activity increases the heart rate and has vasoconstrictive effects that increase blood pressure. Increased parasympathetic activity decreases the heart rate and has vasodilative effects that decrease blood pressure. A positional change to an upright position is normally responded to by an increase in sympathetic output and a decrease in parasympathetic output to compensate for the gravitational effect that displaces blood to the lower extremities. Any failure in this normal reflex can impair cerebral perfusion resulting in syncope.

Because of the numerous etiologies of syncopal events, syncope can go unexplained in many patients, preventing proper treatment. Underlying causes could be life-threatening cardiac conditions. Even when the cause is benign, serious injury can occur due to falling during a syncopal event or if a syncopal event occurs during driving. Recurrent, unpredicatable loss of consciousness can have a profound effect on a patient psychologically and on his or her quality of life.

Evaluation of a patient experiencing syncope can be extensive and costly and include ambulatory ECG (Holter) monitoring, echocardiography, electrophysiologic testing, exercise-tolerance testing, electroencephalography, computed tomography, coronary angiography, glucose-tolerance testing and tilt table testing. Tilt table testing is performed in an attempt to induce a syncopal event by subjecting a patient to a positional change and monitoring the patient's blood pressure and heart rate to determine abnormalities in the autonomic reflex. Conclusive diagnosis may remain elusive even after extensive clinical examination because the precipitating factors leading to a syncopal event may not be present during an examination.

ECG monitoring using an ambulatory device (Holter), does not always reveal a cardiac cause of syncope because a patient may wear a Holter monitor only for a period of one or two weeks, during which no syncopal events occur, and patients may be non-compliant in wearing an external device. Chronic ECG monitoring using a minimally invasive implantable device, such as the Reveal® insertable loop recorder available from Medtronic, Inc., Minneapolis Minn., can be performed for longer periods of time, for more than one year, with little inconvenience to the patient. Such chronic ECG monitoring can reveal cardiac arrhythmias at the time of infrequent, spontaneous syncopal events, allowing a physician to make a diagnosis.

Cardiac arrhythmias, however, may not be the sole or initiating cause of syncope. Hypotensive episodes may precede an arrhythmic event, or be present during sustained normal sinus rhythm, and still lead to syncope or near syncope. Therefore a combination of chronic blood pressure monitoring and ECG monitoring would provide improved diagnostic information for a physician. Such chronic monitoring would be valuable not only in monitoring a patient having unexplained, recurrent syncope but also in patients suspected of having transient arrhythmias, cardiomyopathy or other cardiac conditions, blood sugar fluctuations, respiratory conditions, or other conditions that may manifest in hypotensive or hypertensive episodes. Gathered ECG and blood pressure data can be useful for diagnostic purposes as well as evaluating the effectiveness of a prescribed therapy.

SUMMARY OF THE INVENTION

The present invention provides a minimally invasive, implantable heart sound and ECG monitor and associated method for deriving blood pressure from heart sound data. The device is equipped with an acoustical sensor, preferably a piezoelectric sensor, for detecting pressure waves associated with heart sounds. The analog signals generated by the heart sound sensor are digitized and processed to determine a patient's blood pressure based on custom spectral analysis and processing of the first and second heart sounds.

The device is further equipped with subcutaneous ECG electrodes and a memory for storing ECG and heart sound data. A detected R-wave on a sensed ECG signal may be used to trigger sampling of the heart sound sensor signal for a specified period of time for detecting the first heart sound. A detected T-wave may be used to trigger sampling of the second heart sound signal. Heart sound and ECG data are continuously sampled and stored in a looping memory based on a first-in, first-out basis.

An automatic or manual storage trigger event causes a predetermined interval of ECG and heart sound data stored in temporary looping memory to be stored in a designated area of long-term memory. An automatic trigger may be an arrhythmia detected from the subcutaneous ECG signal. A manual trigger may be delivered during syncope or near-syncope by the patient wearing the implanted device, or another person, using an external device or other manual triggering method.

Spectral analysis of heart sound data is performed to determine a number of spectral variables which may include any of the fundamental frequency and power, second and third harmonics and respective powers, and total harmonic power of the first and second heart sounds. These variables are used in calculating an estimated systolic blood pressure according to a set of best fit equations determined during a calibration method.

The calibration method, which may be performed at the time of device implant or at any time after implantation, includes measuring a patient's blood pressure using a standard clinical method while simultaneously collecting heart sound data. After performing custom spectral analysis of the heart sound signals, regression analysis is performed on spectral variables to identify a set of best fit weighted equations for predicting the measured blood pressure. The equation parameters, e.g. coefficients, constants, exponents, etc., and associated weighting factors are stored for use in calculating estimated blood pressure from stored heart sound data in an individual patient, acquired before or after the calibration procedure.

Preferably, blood pressure estimation from stored heart sound data is performed off-line by an external device after uploading stored data from the implanted device. By storing heart sound data in the implanted device and determining the estimated blood pressure later using an external device, the implantable device may be simplified and minimized in size.

Heart sound and ECG data may also be uplinked to an external device for processing in real-time. Real time processing is particularly useful during calibration procedures and for confirming calibration results. Alternatively, a microprocessor may be included in the implanted device for processing heart sound data and estimating blood pressure.

Concurrent ECG and estimated blood pressure may be displayed on an external device for review by a physician. Chronically monitored blood pressure based on custom heart sound spectral analysis provides a valuable tool for diagnosing an array of clinical conditions.

DETAILED DESCRIPTION OF THE INVENTION

Figure 1:
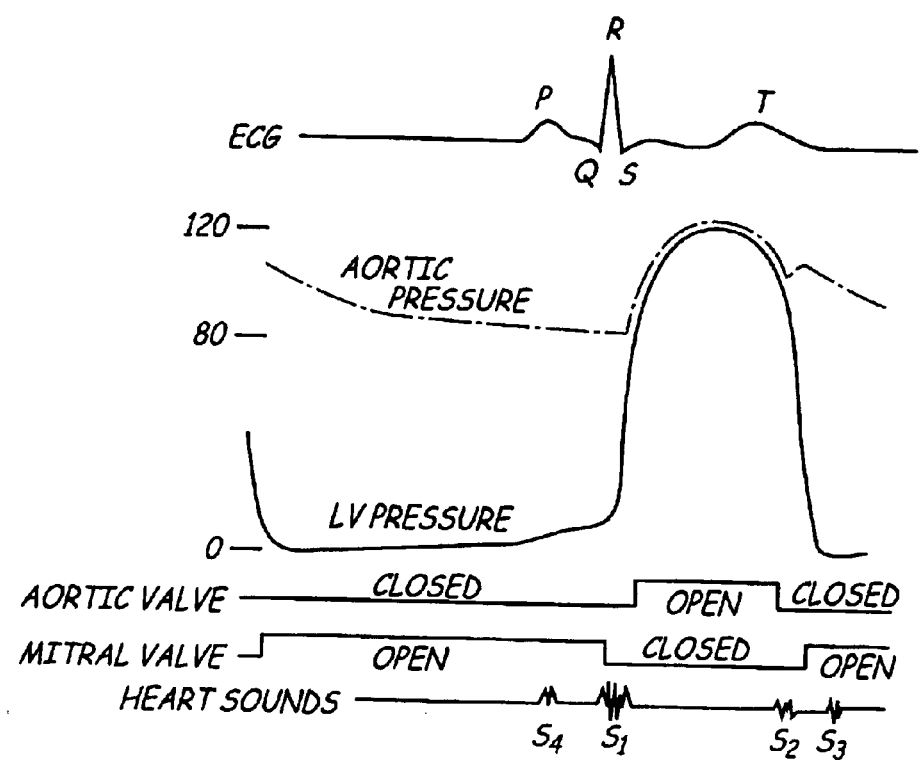
FIG. 1 illustrates the simultaneous ECG events, blood pressure changes and heart sounds that occur in the left ventricle during a cardiac cycle.
Figure 2:
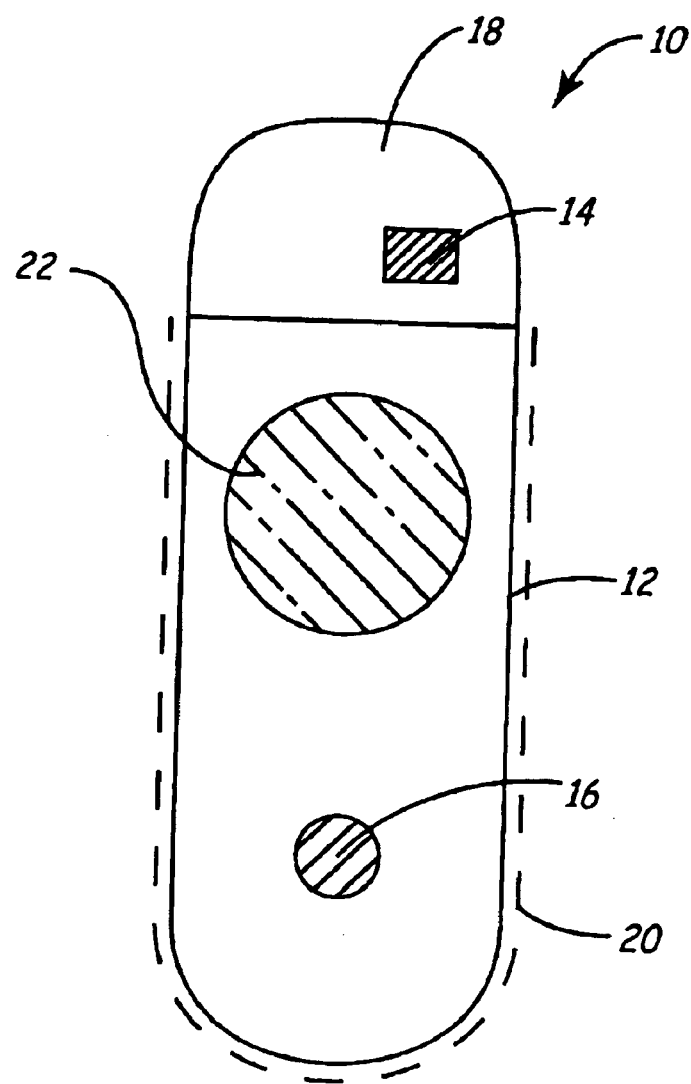
FIG. 2 is a plan view of an implantable device for storing ECG and heart sound data according to the present invention.

FIG. 2 is a plan view of an implantable device 10 for monitoring and storing ECG and heart sound data according to the present invention. The size and shape of device 10 may be provided as generally disclosed in commonly assigned U.S. Pat. No. 5,987,352, issued to Klein, incorporated herein by reference in its entirety. Device 10 is preferably implanted subcutaneously in the general thoracic region. Placement of device 10 near the sternum in the left pectoral region may generally provide good heart sound detection, however, optimal device placement may vary between individuals. An optimal implant site for receiving heart sound signals may be determined on an individual basis prior to implantation of device 10 by performing an examination with a stethoscope. Optimal recording sites for heart sounds in phonocardiography are reviewed in, "Blood pressure and Sound," Chapter 7 in *Medical Instrumentation: Application and Design*, Second Edition, ed. John G. Webster, Houghton Mifflin Company, 1992, pp. 378–407, incorporated herein by reference.

The device 10 is provided with a hermetically sealed housing or "can" 12 preferably formed from a biocompatible metal such as titanium and closed at one end by a plastic cap member 18. Cap member 18 may be formed of materials similar to those used for pacemaker connector blocks, such as polyurethane or epoxy. Housing 12 is provided with an insulative coating 20, indicated by dashed line, formed from an insulating material, such as a Parylene coating. Device 10 is provided with at least two electrodes 14 and 16 for sensing a patient's subcutaneous ECG. Electrode 14 is formed from a biocompatible conductive metal such as platinum, iridium, titanium, or alloys thereof. Electrode 14 may be mounted in cap member 18 with an exposed surface for detecting the patient's ECG and is electrically connected to a conductive feed-through to an internal circuit board. Electrode 16 may be formed as an uninsulated portion of the housing 12 by forming an opening in the insulative coating 20. While the embodiment of device 10 is shown in FIG. 2 having a particular shape and two ECG sensing electrodes, it is recognized that the present invention may be practiced in an implantable device having other shapes and having multiple ECG electrodes. For example, multi-electrode ECG sensing in an implantable monitor is described in U.S. Pat. No. 5,313,953 issued to Yomtov, et al., incorporated herein by reference in its entirety.

Device 10 is further provided with a heart sound sensor 22. Heart sound sensor 22 is preferably formed from a piezoelectric material, which may be a piezoelectric ceramic, film, or polymer. In an alternative embodiment, heart sound sensor 22 may be provided as a miniaturized microphone. However, an advantage of the preferred embodiment is that a piezoelectric material does not require an energizing power supply, allowing the battery size required by device 10 to be minimized, reducing the overall size of device 10. Sensor 22 may be mounted on or within housing 12, and electrically coupled to a circuit board within device housing 12. Alternatively, sensor 22 may be mounted on or within cap member 18 and electrically coupled to an internal circuit board via feedthrough wires. Sensor 22 is preferably hermetically sealed against body fluids, and mounted on a diaphragm or other component that stabilizes the position of sensor 22 while providing good acoustical coupling. A monitor housing including a microphone diaphragm, which may be adapted for use with the present invention, is generally disclosed in the above-cited U.S. Pat. No. 6,409,675, issued to Turcott, incorporated herein by reference in its entirety.

Sensor 22 may be provided as a hard piezoelectric ceramic, a relatively soft piezoelectric ceramic, or a flexible piezoelectric film formed from a piezoelectric polymer such as polyvinylidene fluoride. A soft piezoelectric ceramic such as Model PZT-5A available from Morgan Electro Ceramics, may provide a suitable sensitivity for measuring heart sounds and is currently the preferred embodiment of sensor 22.

Figure 3A:
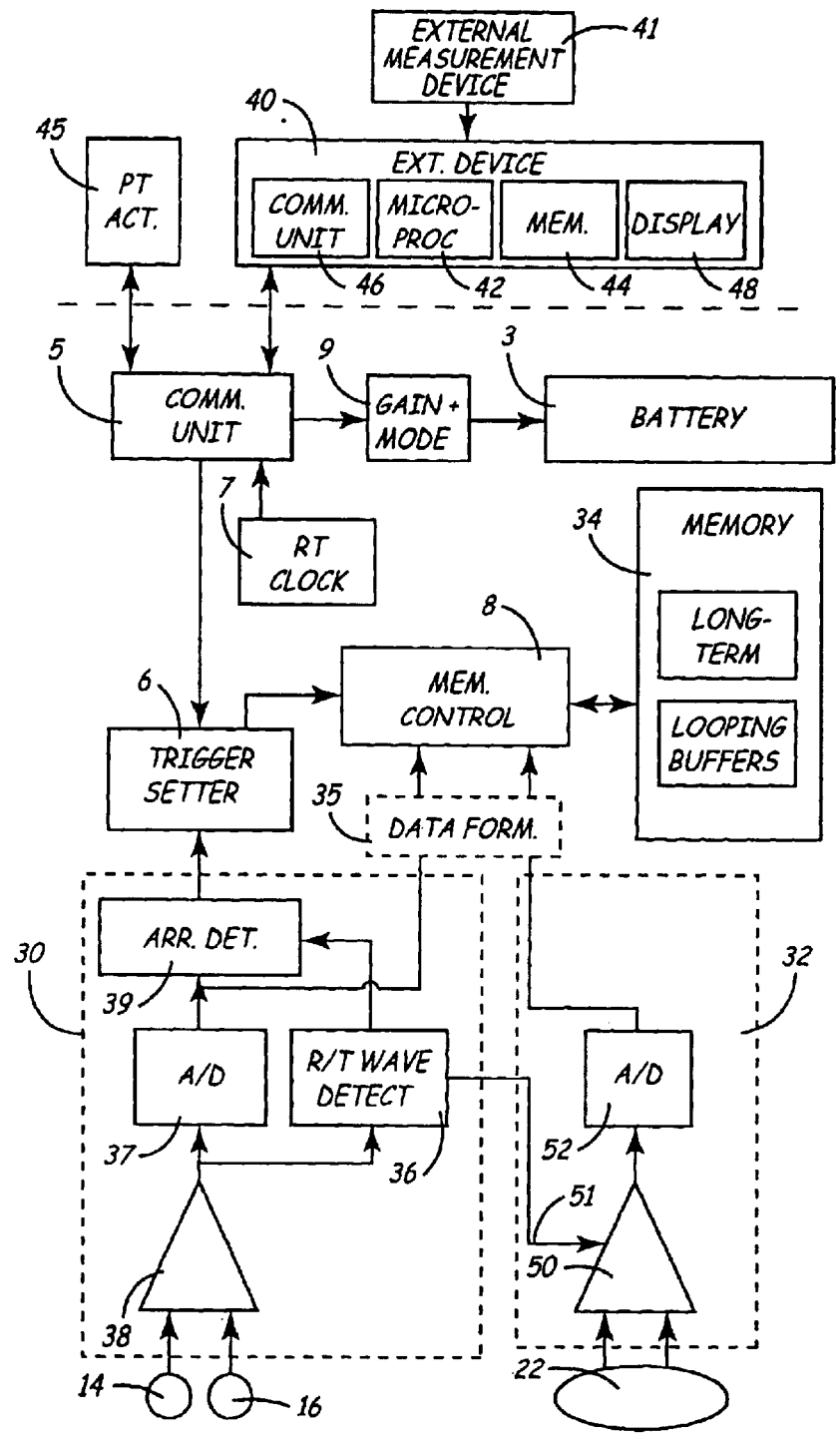
FIG. 3A is a high-level block diagram of circuitry included in the device of FIG. 2.

FIG. 3A is a high-level block diagram of circuitry included in an implantable medical device system including the device 10 of FIG. 2. As illustrated in FIG. 3A, an implantable medical device system according to the present invention includes an external device 40 in communication with device 10. Device 10 includes integrated circuits, powered by battery 3, for performing all device functions. In alternative embodiments, a microprocessor based control system may be included in device 10 for controlling device functions and performing optional onboard data processing. Gain and mode register 9 is provided for storing operational parameter settings, such as amplifier gain settings, sensitivity, sensing window durations, data storage triggering events, etc., for ECG channel 30 and heart sound channel 32. Operational parameters may be programmed in gain and mode register 9 using an external device 40 in communication with device 10 via communications unit 5.

In ECG channel 30, electrodes 14 and 16 bring an ECG signal from the body to an input circuit 38, shown as a differential amplifier for simplicity, the output of which is fed to an R-wave and T-wave detector 36 and an A/D converter 37. Both these circuits 36 and 37 supply output to an arrhythmia detector 39, which in this preferred embodiment supplies an automatic trigger signal to the trigger setting circuit 6. R-wave and T-wave sensing and arrhythmia detection may be performed as generally described in the '352 patent. R-wave and T-wave sensing and arrhythmia detection algorithms known for use in pacemakers and implantable cardioverter defibrillators may alternatively be adapted for use in the present invention.

In heart sound channel 32, input circuit 50 receives signals from heart sound sensor 22. Input circuit 50 is shown as a differential amplifier for the sake of simplicity. Input circuit 50 is enabled by a signal from detector 36 on line 51 indicating detector 36 has detected an R-wave or T-wave. During a predetermined time window following detection of an R-wave and/or T-wave, as set by gain and mode register 9, input circuit 50 is enabled for receiving a signal from sensor 22. A/D converter 52 samples the output from input circuit 50.

Memory control circuit 8 receives data from A/D converters 37 and 52 and/or data from R-wave and T-wave detector 36 and optionally from arrhythmia detection circuit 39. Memory control circuit 8 controls how received data relating to the patient's ECG and heart sounds are stored in memory 34. Memory 34 preferably includes temporary looping memory buffers for storing data temporarily, on a continuous basis, and further includes designated memory partitions for storing data long-term upon an automatic or manual trigger. Long-term data is saved until it is uploaded to an external device 40, after which it may be permanently deleted by a user.

The data output from the A/D converters 37 and 52 may be converted, compressed, formatted and marked or reformulated if desired in a data formulation circuit 35 before the data is ready for input into the memory 34. The memory control circuit 8 receives input from the A/D converters 37 and 52, with or without conversion and so forth from circuit 35, from the arrhythmia detection circuit 39, as well as signals from the trigger setter circuit 6. The trigger setter circuit 6 may also be controlled by a communications unit 5 which operates to receive and decode signals from the outside of the device 10 that are telemetered or otherwise downloaded by a user.

Long-term storage of ECG and heart sound data may be triggered by automatic or manual triggers. Automatic triggers are generated by trigger setting circuit 6 in response to an arrhythmia detection by circuit 39 in a preferred embodiment. Manual triggers are generated by trigger setting circuit 6 in response to an externally applied trigger command. As such, communications unit 5 may receive a signal from an external patient activator 45 for manually triggering long-term data storage. Patient activator 45 may take the form of a handheld device that is battery-powered and uses coded radio-frequency telemetric signals transmitted upon depressing a button, to trigger data storage by the device 10. A patient, or another person nearby, may use the handheld device when the patient feels symptomatic or has become unconscious. A handheld device may alternatively be provided having a magnet that closes a magnetic switch within device 10 when held in the vicinity of device 10 to elicit a data storage trigger signal. Alternative embodiments for a patient activated trigger can include light activation, sonic activation or mechanical activation by finger tapping or slapping. Various modes of patient activated triggering are described in the '352 patent.

If a patient trigger is used it is advantageous to provide feedback to the patient regarding whether the attempt to trigger long-term storage of the event was successful. To accomplish this device 10 should telemeter out a signal that indicates it has recognized a valid trigger. The patient activator 45 then notifies the patient through some known notification mechanism whether the implanted device has been properly triggered. This notification can be one of any combination of a number of notification methods including: one or two visual sources such LED's, an auditory source such as a beeping speaker in one or two tones, or a tactile source such as a vibration. See also U.S. Pat. No. 5,518,001, issued to Snell, incorporated herein by reference, for other potential trigger-indicator ideas for a hand-held patient activated trigger device.

Communications unit 5 includes an antenna or other transceiver device or circuitry to communicate with external device 40 and patient activator 45. Communications unit 5 may receive signals from external device 40 that include operational parameters or indicate that uploading of stored data is requested of device 10. During periodic device 10 interrogations, communications unit 5 will communicate with the memory control circuit 8 to request the uploading of long-term stored data to an external device 40 for analysis. A clock or counter circuit 7 reports the time since start or real time to the outside interrogator device 40 contemporaneously with a data uploading session so that the events recorded in memory 34 may be temporally pinpointed. Additionally, communications unit 5 may receive signals from external device 40 requesting uplinking of ECG and heart sound data in real time.

The external device 40 is preferably a device that is commonly called a "programmer" in the pacemaker art, because it's usual function is to communicate with and program implanted devices. External device 40 preferably includes a microprocessor 42, a memory 44, a communications unit 46, and a display 48. Under the control of microprocessor 40, external device 40 may be used to download programming commands via communication unit 46 to device 10 and receive uploaded ECG and heart sound data. Executable code stored in memory 42 may be run by microprocessor 42 to process uploaded data for calculating estimated blood pressure and displaying blood pressure and concurrent ECG data on display 48. Heart sound data may also be received and processed in real time to allow real time display of a patient's ECG and a running average of the systolic and/or diastolic blood pressure or mean blood pressure derived from the heart sound data. Both graphic and numeric displays of concurrent ECG and average blood pressure may be displayed. Alternatively, heart sound and ECG data may be saved to a disk and methods for estimating and displaying blood pressure results, as will be described below, may be executed on a personal computer.

In addition, external device 40 also receives patient blood pressure data resulting from measurements made using standard clinical methods, such as a blood pressure cuff or an indwelling pressure catheter, for example, via an external measurement device 41. The patient blood pressure data received via external measurement device 41 is used to calibrate heart sound signals, as described below.

Figure 3B:
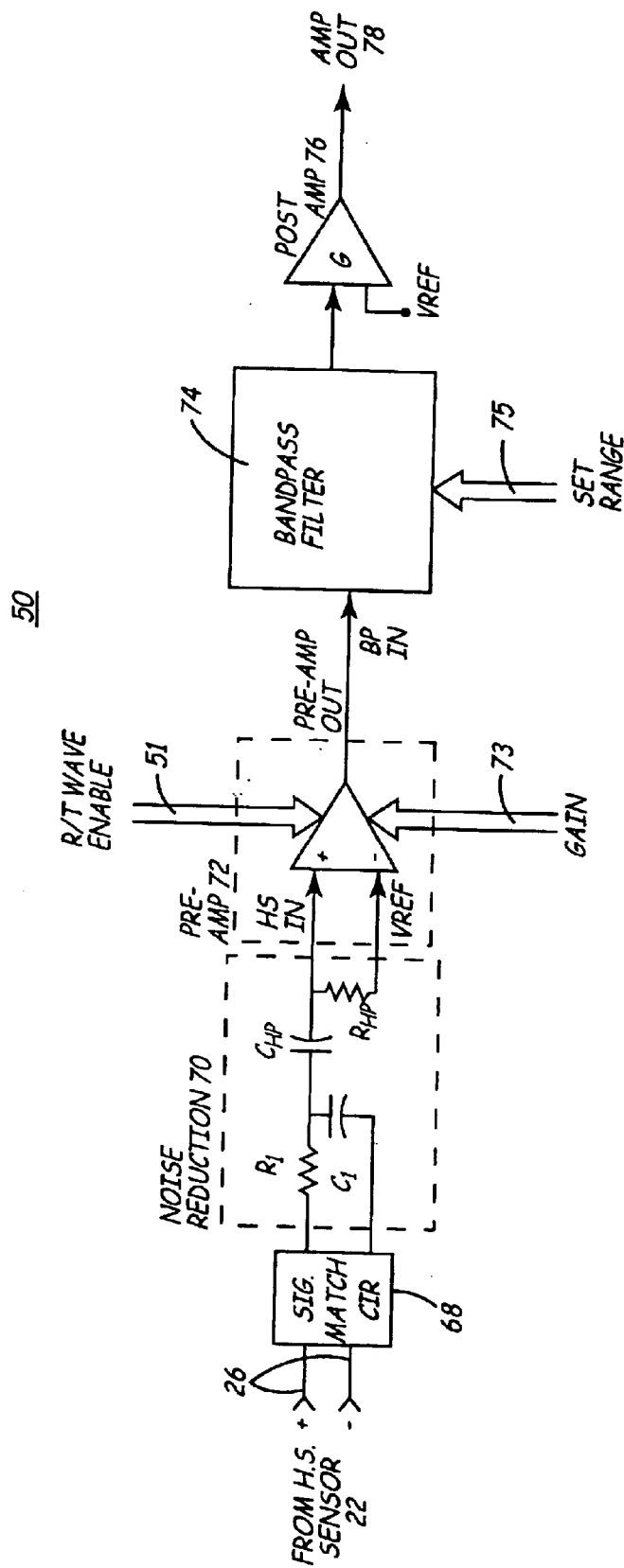
FIG. 3B is a circuit diagram depicting components that may be included in heart sound sensor input circuit included in the FIG. 3A.

FIG. 3B is a circuit diagram depicting components that may be included in heart sound sensor input circuit 50. Signals from sensor 22 may first be received on signal lines 26 and 24 by an optional signal matching circuit 68. Signal matching circuit 68, which may be a voltage divider, can be included in heart sound sensor input circuit 50 if impedance matching is required for matching the signal from sensor 22 to the remaining filter and amplifier circuitry of heart sound sensor input circuit 50. The output of the signal matching circuit 68 if present, or alternatively the signal lines 26 and 24, may be fed directly into noise reduction circuitry 70 for eliminating or reducing noise associated with respiration, voices, muscle noise, or other sounds. Noise reduction circuitry 70 may include a resistor $R_1$ and capacitor $C_1$ for eliminating intermittent or high frequency signals associated with extraneous sounds and optional capacitor $C_{HP}$ and $R_{HP}$ to reduce very low frequency noise. Preamplifier 72 receives the output from the noise reduction circuit and may be provided as a differential amplifier having a fixed or programmable gain, received on input line 73. The preamplifier circuit 72 may be enabled for a predetermined window of time, which may be fixed or programmable, upon receiving an R-wave detection signal and/or a T-wave detection signal on signal line 51.

The preamplifier output is provided as input to a bandpass filter 74, preferably tuned, via signal line 75, to pass a range of frequencies containing pertinent heart sound information. The first heart sound typically has a frequency on the order of 25 to 45 Hz and the second heart sound typically has frequency on the order of 50 Hz. Therefore bandpass filter 74 may be tuned to a range on the order of 10 Hz to 100 Hz, and more preferably to a range on the order of 20 Hz to 60 Hz, though systolic blood pressure estimation based on heart sound data collected below 32 Hz is feasible. Tuning of bandpass filter 74 may be programmable to allow a selected frequency range to be tailored to obtain the best signal for an individual patient.

Bandpass filter output is received as input to an end stage main amplifier 76, which may have a fixed or programmable gain. Amplifier 76 may also be provided as an automatic gain control amplifier. The use of automatic gain control amplifiers is generally described in U.S. Pat. No. 5,117,824, by Keimel, et al., incorporated herein by reference in its entirety. The output of main amplifier 76 is provided to A/D converter 52 and signal processing circuitry 52 as shown previously in FIG. 3A.

Figure 4:
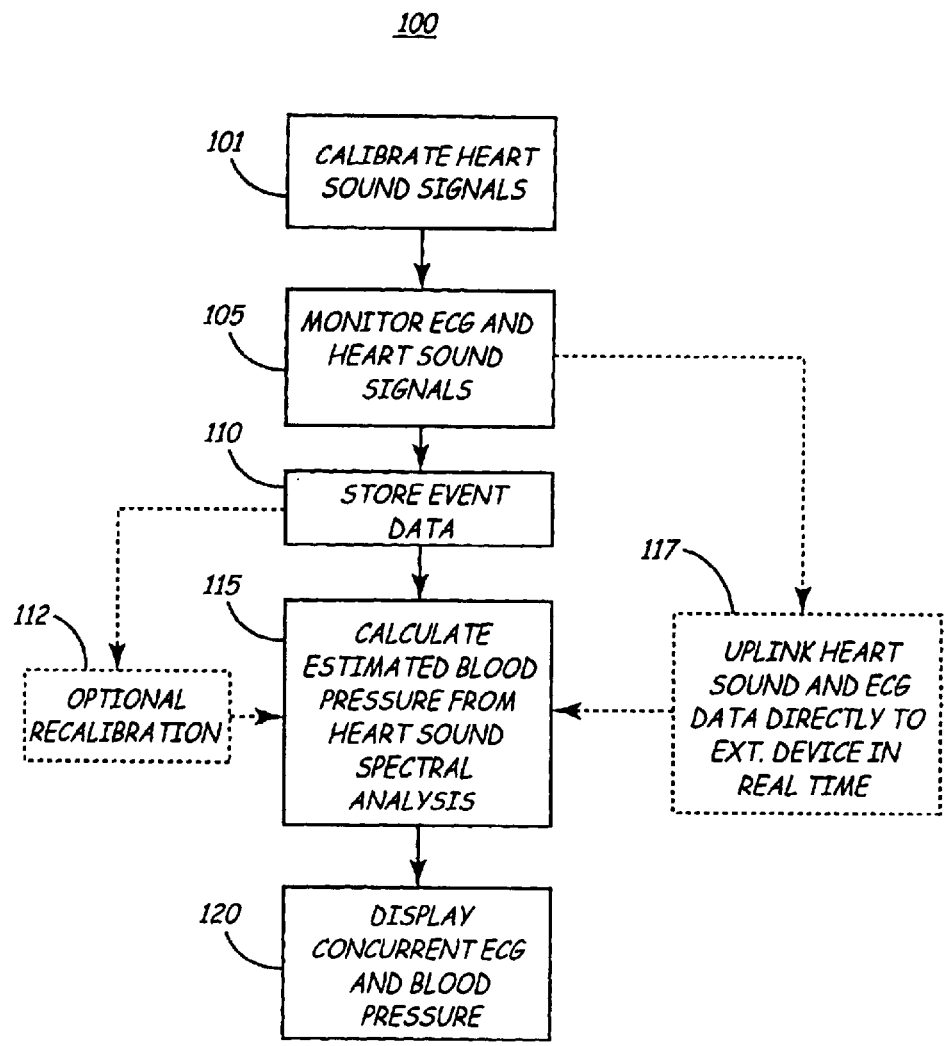
FIG. 4 is a flow chart providing an overview of a method for chronically monitoring blood pressure estimated from the spectral analysis of heart sound signals.

FIG. 4 is a flow chart providing an overview of a method for chronically monitoring blood pressure estimated from a custom spectral analysis and processing of heart sound signals. At step 101, heart sound signals sensed by sensor 22 in device 10 are calibrated to blood pressure measurements made using a standard clinical method. Calibration methods will be described in greater detail below, in conjunction with FIG. 6. After calibrating, ECG and heart sound signals are monitored continuously at step 105 by device 10. Upon an event trigger, heart sound and ECG data are stored long-term in the memory of device 10 for later processing and analysis. Heart sound and ECG data may also be directly uplinked to an external device in real time at step 117 for immediate analysis and display. Real-time analysis and display are particularly useful for verifying calibration.

Estimated blood pressure is calculated at step 115 based on the spectral analysis of heart sound data. Blood pressure calculations are preferably performed by an external device 40 after uplinking stored or real-time data from the implanted device 10 to minimize the microprocessing and power requirements of device 10. Re-calibration of heart sound signals may optionally be performed at step 112 prior to calculating the estimated blood pressure at step 115. Re-calibration may improve the accuracy of blood pressure estimation, particularly if considerable time has passed since the original calibration was performed or if other conditions have changed that may affect the calibration such as patient weight gain or loss.

A preferred method for calculating an estimated systolic blood pressure, at step 115, based on custom spectral analysis of first and second heart sounds will be described in detail below. It is expected that calculation methods may be modified to calculate a mean or diastolic pressure based on the spectral analysis of the first and/or second heart sounds. The estimated blood pressure and the concurrent ECG signal may be displayed graphically on display 48 at step 120. A numeric value of a running average blood pressure and a numeric value of the heart rate determined from the ECG may alternatively or additionally be displayed.

Figure 5:
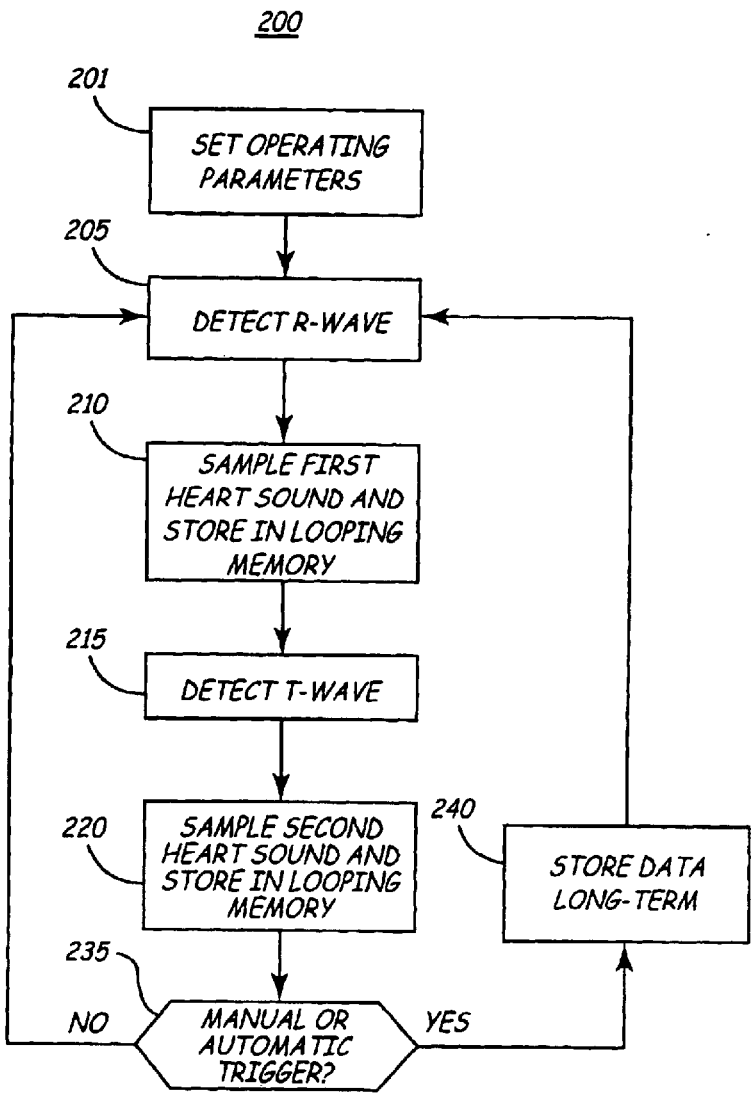
FIG. 5 is a flow chart summarizing the steps in a method performed by the device of FIG. 2 for acquiring heart sound data for use in deriving blood pressure.

FIG. 5 is a flow chart summarizing the steps in a method performed by device 10 for monitoring and acquiring heart sound data for use in deriving a blood pressure. Method 200 begins at step 201 by setting operating parameters. Operating parameters may include fixed or programmable settings related to acquisition, processing and storing of heart sound data. Parameters include a first heart sound ($S_1$) sensing window duration that is triggered by detection of an R-wave by R-wave and T-wave detector 36, and a second heart sound ($S_2$) sensing window duration that is triggered by detection of a T-wave by detection circuit 36. During the $S_1$ and $S_2$ sensing windows, input circuit 50 is enabled for receiving signals related to heart sounds received by heart sound sensor 22. $S_1$ is typically on the order of 150 ms in duration, and $S_2$ is typically on the order of 120 ms in duration. The associated sensing windows may therefore be set on the order of 100 to 200 ms, more preferably on the order of 150 ms in duration. Both $S_1$ and $S_2$ sensing windows may be set to the same duration, or they may be set at different durations.

Other operating parameters set at step 201 may include gain settings for amplifiers included in input circuit 50. If blood pressure estimation is performed by device 10, parameters used in calculating estimated blood pressure from acquired heart sound data may also be set at step 201 based on calibration methods to be described below.

At step 205, method 200 waits for an R-wave to be detected by detection circuit 36. Upon an R-wave detection, input circuit 50 is enabled at step 210 and a signal associated with the first heart sound is sampled and digitized by A/D converter 52. At step 215, method 200 waits for detection of a T-wave by detection circuit 36. Input circuit 50 is enabled at step 220 and a signal associated with the second heart sound is sampled and digitized by A/D converter 52. A sampling rate on the order of 100 Hz is feasible, but higher sampling rates may be preferred for obtaining better frequency resolution and thus potentially more accurate or more precise blood pressure estimations. Better frequency resolution, however, comes with a trade-off of either increased device size due to greater memory capacity requirements or a reduced number or shorter duration of data episodes capable of being stored in long-term memory.

The digitized heart sound data may be stored temporarily in a designated area of memory 34, under the control of memory control 8. If an automatic or manual data storage trigger event occurs, ECG and heart sound data stored in temporary memory are stored long-term at step 240 in a designated area of memory 34 to be saved until device 10 is interrogated by external device 40 for uploading of stored data. Acquired data is stored for a predetermined interval of time such that a segment of data occurring before the trigger event and a segment of data after the trigger event is included in the stored data.

Method 200 is executed continuously by repeating steps 205 through 235 such that ECG and heart sound data are stored on a beat-by-beat basis in temporary looping memory buffers. At any time, a manual or automatic trigger causes device 10 to save a predetermined interval of ECG and heart sound data in long-term memory. In one embodiment, operational modes for data storage triggering is programmable to allow patient triggering only and/or one or more types of automatic triggers for data storage. An interval of data, preferably on the order of 21 minutes is stored which includes data stored in the temporary memory buffers prior to the trigger event and data following the trigger event.

Depending on the long-term memory capacity, a limited number of triggered events may be stored between uploading data sessions. Preferably at least three events of approximately 7 minutes each (on the order of 21 minutes total) may be stored. Additional triggered events may overwrite the oldest stored event if uploading has not occurred and long-term memory is full. Increased memory capacity would allow for longer event episodes or a greater number of events to be stored. The number of events that may be stored may also be increased by storing data in a compressed format. Data compression may be at a compression ratio of 2:1 or some other device supported ratio. When setting the operational mode of the device, the physician or attendant can decide whether to record data in a compressed mode or not. If better time resolution of ECG or acoustical data is required than available from compressed data storage, the physician should select non-compressed recording, thereby limiting the time available to record. In some embodiments the sampling rate may be modified as well, for both ECG sampling and heart sound data sampling. Many types of known compression algorithms could be used. An excellent example is found in the article Arrhythmia Detection Program for an Ambulatory ECG Monitor by Mueller, copyright 1978, ISA, ISBN 876645, incorporated herein by reference in its entirety.

Increased time resolution of heart sound data may be desired for more precise estimation of blood pressure. Therefore in one embodiment, a higher sampling rate may be selected, for example on the order of 200 Hz. In order to store the same duration of data acquired at the higher sampling rate, the memory capacity would need to be increased accordingly. In addition, battery current drain would be increased by the higher sampling rate, shortening the device longevity or requiring a larger battery, increasing overall device size.

Figure 6:
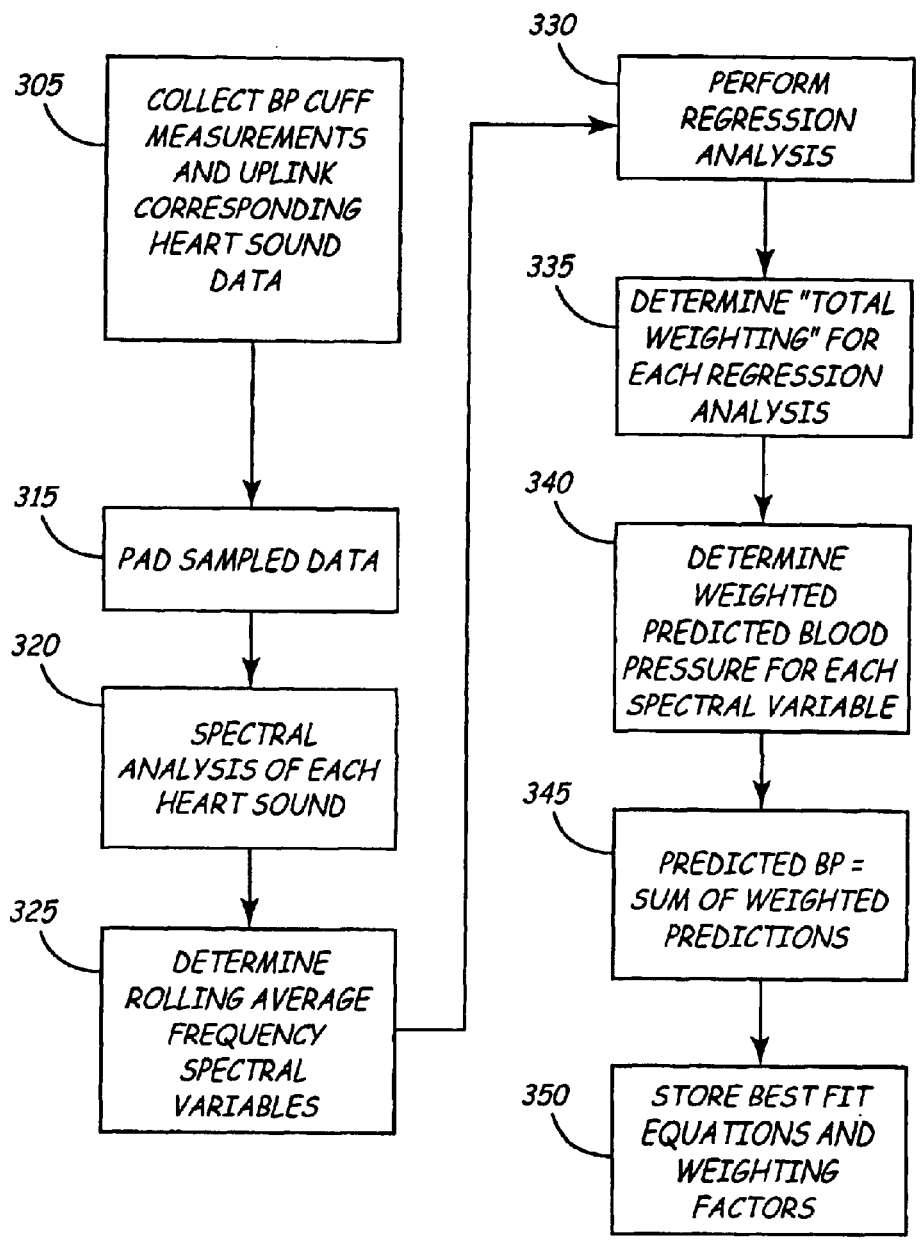
FIG. 6 is a flow chart summarizing a calibration method for determining a set of best fit equations to be used in calculating an estimated blood pressure from the spectral analysis of heart sound signals in an individual patient.

FIG. 6 is a flowchart summarizing a method for calibrating the heart sound signals for estimating blood pressure in an individual patient in accordance with the present invention. The calibration method 300 may be performed at the time of device 10 implant and may be repeated at any time after implantation to maintain accuracy of blood pressure estimates despite possible calibration drift due to factors such as device wander or patient weight gain or loss. At step 305, a patient's blood pressure is measured using a standard clinical method, such as using a blood pressure cuff or an indwelling pressure catheter and input to external device 40 via external measurement device 41. During blood pressure measurements, heart sound data is sampled and uplinked in real time to external device 40. Heart sound data may alternatively be stored in long-term memory during a series of blood pressure measurements and subsequently be uplinked to external device 40. A manual trigger may be used to store heart sound data at the time of a blood pressure measurement. In a preferred method, multiple blood pressure measurements are made under varying conditions to allow heart sound data to be collected at different blood pressures. For example, blood pressure measurements and heart sound data may be recorded at rest and during drug and/or exercise-induced hypertension. Preferably at least five different blood pressures are measured ranging from a patient's resting blood pressure to a maximum blood pressure encountered during a stress test, for example during a 10 minute exercise stress test.

After collecting the calibration data, the stored heart sound data is uplinked to external device 40 at step 315. The sampled data is preferably padded to increase the frequency resolution for performing custom spectral analysis. When data is stored at a preferred sampling rate of 100 Hz for 150 ms for each heart sound, 16 sample points are collected and preferably padded to increase the number of data points to 8192 using a data point slope method. Generally, this method uses a linear fit of two consecutive data points to interpolate a number of intervening data points, thereby artificially increasing the sampling rate. In the present example, 16 sample points are increased to 8192 points by interpolating 512 points linearly between each pair of consecutively sampled points, increasing the real sampling rate of 100 Hz to an artificial rate of 51,200 Hz.

At step 320, custom spectral analysis is performed on each of the first and second heart sounds for each cardiac cycle stored in a given episode. A number of spectral variables based on the fundamental frequency, $f_0$, and second and third harmonics, $f_2$ and $f_3$, and their associated powers ($P_0$, $P_2$ and $P_3$), the total harmonic power (THP), and the total harmonic distortion (THD) are determined. The spectral variables determined preferably include all or any subset of, but are not limited to, the 24 spectral variables listed in Table I below. A running average for each variable is determined at step 325 from a given number of consecutive cardiac cycles, preferably 7 cardiac cycles. By determining a running average for each spectral variable, the effect of noise, e.g. due to breathing, voice, skeletal or muscle motion, etc., is reduced. A processed data set for each measurement episode now includes a sequence of running averages for each spectral variable.

Table I. Spectral Analysis Variables determined for each cardiac cycle during calibration and blood pressure estimation.

S1 and S2 Average Total Harmonic Power
S1 and S2 Average Frequency Ratio A ($f_3/f_0$)
S1 and S2 Average Power Ratio A ($P_0$/THP)
S1 and S2 Average Ratio B (($P_0+P_3$)/THP)
S1 and S2 Average Power Ratio C ($P_3/P_0$)
S1 and S2 Average Peak Power
S1 and S2 Average Peak Frequency
S1 Total Harmonic Power
S1 Frequency Ratio A ($f_3/f_0$)
S1 Power Ratio A ($P_0$/THP)
S1 Power Ratio B (($P_0+P_3$)/THP)
S1 Power Ratio C ($P_3/P_0$)
S1 Peak Power (PP)
S1 Peak Frequency (PF)
S2 Total Harmonic Power
S2 Frequency Ratio A ($f_3/f_0$)
S2 Power Ratio A ($P_0$/THP)
S2 Power Ratio B (($P_0+P_3$)/THP)
S2 Power Ratio C ($P_3/P_0$)
S2 Peak Power (PP)
S2 Peak Frequency (PF)
S1 and S2 Average Total Harmonic Distortion (THD)
S1 Total Harmonic Distortion (THD)
S2 Total Harmonic Distortion (THD)

At step 330, regression analysis is performed on the processed data set to determine a best fit curve for the measured blood pressures as a function of each of the spectral variables. Multiple regression analyses may be performed for each spectral variable, including linear, logarithmic, power, exponential, and polynomial regressions, to determine the analysis producing the highest correlation. A correlation coefficient, $r^2$, for each regression analysis of each spectral variable is determined. The sum of the correlation coefficients for all spectral variables for a given regression analysis is determined as the total significance weighting (TSW) for that particular regression analysis, step 335. The regression analysis having the highest total significance weighting is determined as the best fit analysis for calibrating the heart sound data to actual blood pressure.

Based on the best fit analysis, a weighted predicted blood pressure value is determined for each spectral variable, step 340. The weighted predicted blood pressure is the blood pressure calculated from the best fit equation for a single spectral variable multiplied by the ratio of the correlation coefficient for that variable divided by the total significance weighting for the best fit analysis. For example, if a linear regression analysis produces the highest total significance weighting, a weighted predicted blood pressure based on the linear regression analysis of a spectral variable is given by Equation 1:

$$WBP(P_i) = \frac{r_i^2}{TSW}\{a_i P_i + c_i\} \quad (1)$$

wherein $WBP(P_i)$ is the weighted predicted blood pressure based on the $i^{th}$ spectral variable, $P_i$; $r_i^2$ is the correlation coefficient for a linear regression analysis of $P_i$; TSW is the total significance weighting (sum of all correlation coefficients) for the linear regression analysis of all spectral variables; and $a_i$ and $c_i$ are the x coefficient and constant determined by the linear regression analysis of $P_i$.

The predicted blood pressure determined at step 345 is the sum of the weighted predicted values for each spectral variable as given by Equation 2:

$$BP_{predicted} = \sum_{i=1}^{n} WBP(P_i). \quad (2)$$

Based on preliminary studies, the predicted blood pressure is expected to be within approximately 2% to 15% of the measured blood pressure. Even when the predicted blood pressure is less accurate than more invasive direct blood pressure measurement methods, the predicted blood pressure is expected to be repeatable, in part due to the stability of the device 10 implant position and monitoring site, allowing precise measurements of changes in blood pressure.

At step 350, parameters defining the best fit equations, e.g. values for coefficients, constants and/or exponents, determined for each spectral variable and the associated weighting factors are stored for use in estimating blood pressure for an individual patient. In one embodiment, only the parameters defining the equations for the regression analysis having the highest total significance weighting are stored. In other embodiments, multiple regression analysis equations and weighting factors may be stored to allow multiple blood pressure estimates to be determined. The equations and weighting factors may be stored in the memory of an external device such that all blood flow estimates are determined off line after uploading stored data to the external device. Alternatively, equations and weighting factors may be downloaded to the implanted device 10 and stored in memory 34. Processing of stored heart sound data and estimation of blood pressure may then be performed immediately after a triggering event or in real time by device 10. However, it is recognized that the processing power required to calculate an estimated blood pressure will require considerable microprocessing time and battery energy. In order to minimize the size of device 10, therefore, a more practical and preferred implementation is to post-process stored heart sound data after uploading the data to an external device.

Figure 7:
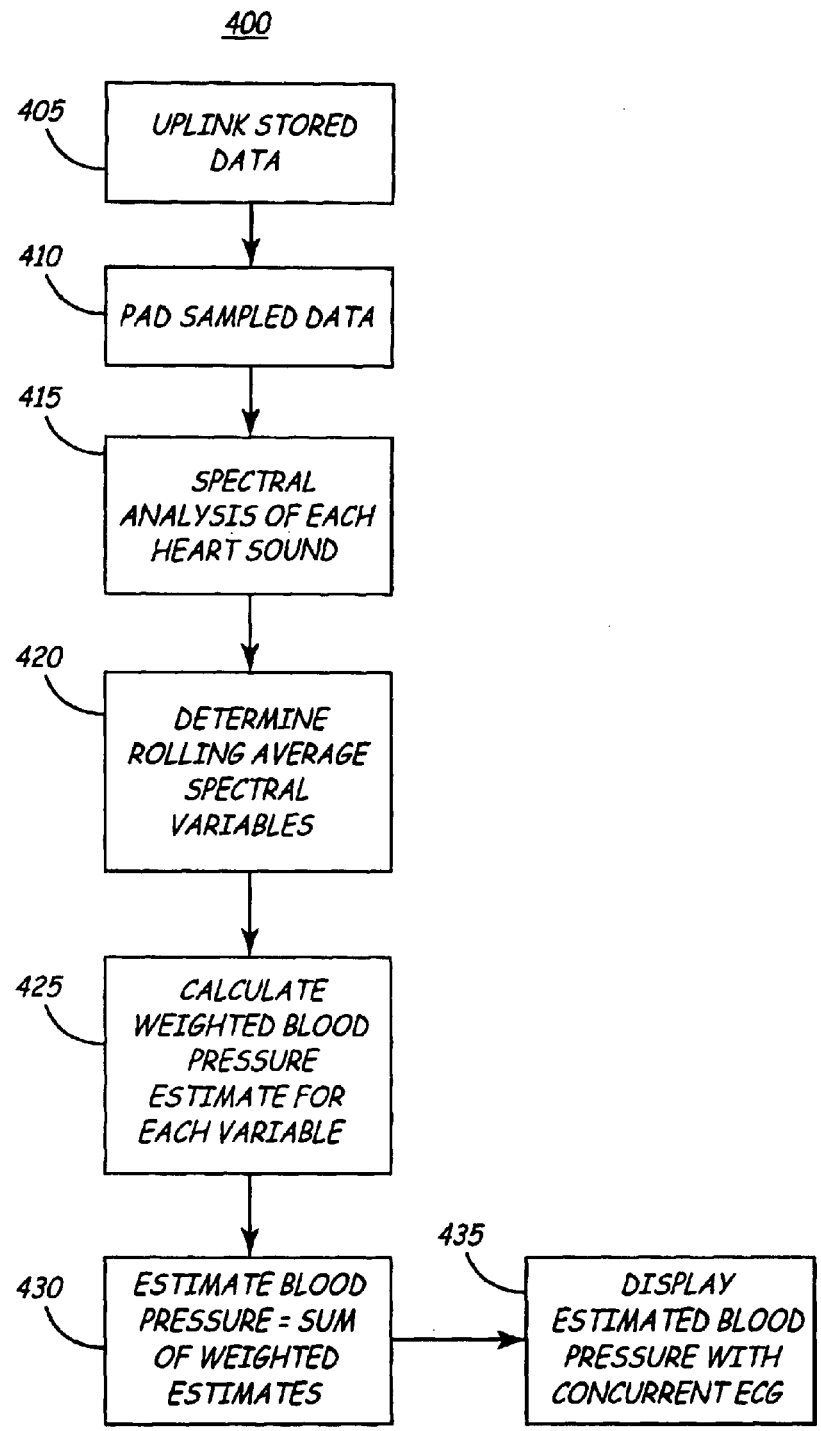
FIG. 7 is a flowchart summarizing a method for calculating estimated blood pressure from heart sound data according to the present invention.

FIG. 7 is a flow chart summarizing a method for calculating an estimated blood pressure based on stored heart sound data. After uplinking stored data at step 405 to an external device, the data may be padded at step 410 to improve frequency resolution as described above. At step 415, spectral analysis of each heart sound is performed to determine the spectral variables used during the calibration methods associated with the first and second heart sounds. Rolling averages of first and second heart sound variables from seven consecutive cardiac cycles are determined at step 420.

For each rolling average value, a weighted blood pressure estimate is calculated at step 425 using the stored best fit equation parameters for the given variable and the associated weighting factor. At step 430, an estimated blood pressure is calculated as the sum of the weighted blood pressure estimates. The calculation of an estimated blood pressure may be summarized by Equation 3:

$$BP = \sum_{i=1}^{n} \frac{r_i^2}{TSW}(f(P_i)) \quad (3)$$

wherein BP is the estimated blood pressure; $r_i^2$ is the correlation coefficient used as the weighting factor associated with the $i^{th}$ spectral variable determined previously during calibration; TSW is the total significance weighting determined previously during calibration for the given regression analysis; and $f(P_i)$ is the best fit equation for the $i^{th}$ spectral variable, $P_i$, determined during the calibration regression analysis.

Thus, a "rolling" blood pressure estimate may be calculated for each cardiac cycle based on the rolling averages determined for seven consecutive cardiac cycles. A tabular or graphical display of the estimated blood pressure results is provided at step 435. The "rolling" blood pressure estimate may be displayed versus time with concurrent ECG data to allow a physician to review ECG and blood pressure events simultaneously.

A minimally invasive ECG and heart sound monitor has thus been described with an associated method for deriving an estimated blood pressure from custom spectral analysis and processing of the first and second heart sounds. Chronic blood pressure monitoring using the device and methods included in the present invention provides a physician with a valuable diagnostic tool. Embodiments described herein are considered exemplary and should not be taken as limiting with regard to the following claims.

We claim:

1. A method for deriving an estimated blood pressure of a patient, comprising the steps of:
   sensing first heart sound signals;
   generating blood pressure estimation parameters in response to the first heart sound signals;
   sensing second heart sound signals and cardiac depolarizations corresponding to the second heart sound signals; and determining an estimated blood pressure in response to the second heart sound signals, the cardiac depolarizations corresponding to the second heart sound signals, and the generated blood pressure estimation parameters.

2. The method of claim 1, wherein the step of determining an estimated blood pressure further comprises performing spectral analysis of the second heart sound signals.

3. The method of claim 1, further comprising repeating the steps of sensing first heart sound signals and generating blood pressure estimation parameters prior to the step of determining an estimated blood pressure.

4. The method of claim 1, further comprising uplinking data corresponding to the second heart sound signals and the cardiac depolarizations corresponding to the second heart sound signals to an external device, wherein the step of determining an estimated blood pressure is performed at the external device.

5. The method of claim 1, further comprising the step of simultaneously displaying the determined estimated blood pressure and corresponding cardiac depolarizations.

6. The method of claim 1, wherein the step of sensing second heart sound signals further comprises generating operating parameters corresponding to acquisition, processing and storing of the subsequently sensed cardiac signals.

7. The method of claim 1, wherein the step of sensing second heart sound signals further comprises the steps of:
generating a first heart sound sensing time period and a second heart sound sensing time period;
detecting an R-wave and a T-wave;
sensing a third heart sound signal within the first heart sound sensing time period in response to the detected R-wave;
sensing a fourth heart sound signal within the second heart sound sensing time period in response to the detected T-wave;
detecting a trigger event; and
storing data corresponding to the third heart sound signal and the fourth heart sound signal in response to the detected trigger event.

8. The method of claim 7, wherein the data corresponding to the third heart sound signal and the fourth heart sound signal is stored in one of long-term memory and short-term memory.

9. The method of claim 1, wherein the step of generating blood pressure estimation parameters comprises:
determining the patient's blood pressure using an external measuring device;
sampling heart sound data corresponding to the determined blood pressure;
performing spectral analysis of the sampled heart sound data;
determining spectral variables;
determining a running average for each of the variables from a predetermined number of cardiac cycles;
perform a best fit analysis to generate a best fit curve for the determined blood pressure as a function of spectral variables; and determining a weighted predicted blood pressure value in response to the best fit analysis.

10. The method of claim 1, wherein the step of determining an estimated blood pressure comprises:
performing spectral analysis of the second heart sounds;
determining rolling average spectral variables;
calculating a weighted blood pressure for each of the variables; and
calculating the estimated blood pressure in response to the calculated weighted blood pressure.

11. An implantable medical device system for deriving an estimated blood pressure of a patient, comprising:
a first sensing portion sensing cardiac depolarizations; a second sensing portion sensing heart sounds and generating corresponding heart sound signals including first heart sound signals and second sound heart signals;
a storage device;
a control circuit receiving data from the first sensing portion and the second sensing portion and controlling storage of the sensed cardiac depolarizations and the heart sound signals in the storage device;
an external device receiving the sensed cardiac depolarizations and the heart sound signals from the storage device, generating blood pressure estimation parameters in response to the first heart sound signals, and determining an estimated blood pressure in response to the second heart sound signals, the cardiac depolarizations corresponding to the second heart sound signals, and the generated blood pressure estimation parameters.

12. The system of claim 11, wherein the external device performs spectral analysis of the second heart sound signals.

13. The system of claim 11, wherein the external device re-generates the blood pressure estimation parameters prior to determining the estimated blood pressure.

14. The system of claim 11, further comprising a display device positioned at the external device simultaneously displaying the determined estimated blood pressure and corresponding cardiac depolarizations.

15. The system of claim 11, wherein the external device monitors the second heart sound signals and the cardiac depolarizations corresponding to the second heart sound signals, and generates resulting operating parameters corresponding to acquisition, processing and storing of the subsequently sensed cardiac signals.

16. The system of claim 11, further comprising an event trigger device transmitting a trigger signal to the control circuit and the external device, wherein the cardiac depolarizations sensed by the first sensing device include an R-wave and a T-wave, and wherein the external device generates a first heart sound sensing time period and a second heart sound sensing time period, the second sensing portion senses a third heart sound signal within the first heart sound sensing time period in response to the sensed R-wave and a fourth heart sound signal within the second heart sound sensing time period in response to the sensed T-wave, and the control circuit stores data corresponding to the third heart sound signal and the fourth heart sound signal in response to the trigger signal.

17. The system of claim 16, wherein the storage device includes long-term memory and short-term memory, and the data corresponding to the third heart sound signal and the fourth heart sound signal is stored in one of the long-term memory and the short-term memory in response to the trigger signal.

18. The system of claim 11, further comprising an external measuring device to generate a measurement of blood pressure externally from the patient, wherein the external device receives the external blood pressure measurement from the external measuring device, samples heart sound data corresponding to the external blood pressure measurement, performs spectral analysis of the sampled heart sound data, determines spectral variables and a running average for each of the variables from a predetermined number of cardiac cycles, performs a best fit analysis to generate a best fit curve for the determined blood pressure as a function of spectral variables, and determines a weighted predicted blood pressure value in response to the best fit analysis.

19. The system of claim 11, wherein the external device perfors spectral analysis of the second heart sounds, determines rolling average spectral variables, calculates a weighted blood pressure for each of the variables, and determines the estimated blood pressure in response to the calculated weighted blood pressure.

20. An implantable medical device system for deriving an estimated blood pressure of a patient, comprising:

means for sensing first heart sound signals;

means for generating blood pressure estimation parameters in response to the first heart sound signals;

means for sensing second heart sound signals and cardiac depolarizations corresponding to the second heart sound signals; and means for determining an estimated blood pressure in response to the second heart sound signals, the cardiac depolarizations corresponding to the second heart sound signals, and the generated blood pressure estimation parameters.

* * * * *